United States Patent [19]

Hisaki et al.

[11] Patent Number: 4,874,773

[45] Date of Patent: Oct. 17, 1989

[54] 3-AMINOCARBONYL-1,4-DIHYDROPYRIDINE-5-CARBOXYLIC ACID COMPOUNDS, AND PHARMACEUTICAL COMPOSITION CONTAINING THE SAME

[75] Inventors: Masakatu Hisaki, Hikone; Kenichi Kashima, Fujiidera; Yasuhiko Sakamoto, Habikino; Masakazu Hojo, Kyoto; Osamu Katayama, Kusatsu; Hiroyoshi Hata, Yokohama, all of Japan

[73] Assignee: Nippon Shoji Kabushiki Kaisha, Osaka, Japan

[21] Appl. No.: 239,005

[22] Filed: Aug. 30, 1988

Related U.S. Application Data

[63] Continuation of Ser. No. 920,124, Oct. 17, 1986, abandoned.

[30] Foreign Application Priority Data

Oct. 21, 1985 [JP] Japan .................. 60-235909

[51] Int. Cl.$^4$ .................. C07D 211/86; A61K 31/455
[52] U.S. Cl. ..................................... 514/355; 546/316
[58] Field of Search .................. 546/316; 514/355

[56] References Cited

U.S. PATENT DOCUMENTS 4,472,411 9/1984 Hatayama et al. .................. 546/321

FOREIGN PATENT DOCUMENTS 2228377 1/1974 Fed. Rep. of Germany .
29989 8/1980 Japan .
20953 5/1982 Japan .
146565 9/1983 Japan .
116267 7/1984 Japan .
227860 12/1984 Japan .
7255 1/1986 Japan .

Primary Examiner—Jane T. Fan
Attorney, Agent, or Firm—Wegner & Bretschneider

[57] ABSTRACT

Novel 3-aminocarbonyl-1,4-dihydropyridine-5-carboxylic acid compounds of the formula:

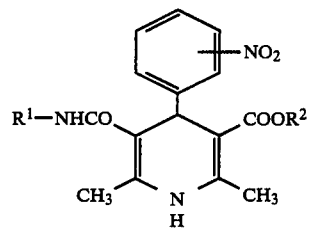

[I]

wherein $R^1$ is H, $C_{1-5}$ alkyl, $C_{2-5}$ alkenyl, $C_{3-5}$ alkynyl, $C_{3-8}$ cycloalkyl, $R^2$ is $C_{1-10}$ alkyl, and the $NO_2$ group is substituted at ortho- or meta-position, provided that when the $NO_2$ group is substituted at ortho-position and $R^2$ is methyl, $R^1$ is $C_{3-5}$ alkyl, $C_{2-5}$ alkenyl, $C_{3-5}$ alkynyl, or $C_{3-8}$ cycloalkyl, and when the $NO_2$ group is substituted at meta-position and $R^1$ is H, $R^2$ is $C_{3-10}$ alkyl, which have excellent hypotensive, vasodilating activities and are useful for the prophylaxis and treatment of hypertension, ischemic heart diseases and cerebral and peripheral circulation diseases.

12 Claims, No Drawings

3-AMINOCARBONYL-1,4-DIHYDROPYRIDINE-5-CARBOXYLIC ACID COMPOUNDS, AND PHARMACEUTICAL COMPOSITION CONTAINING THE SAME

This application is a file wrapper continuation of U.S. application Ser. No. 920,124, filed Oct. 17, 1986 now abandoned.

This invention relates to novel 3-aminocarbonyl-4-dihydropyridine-5-carboxylic acid compounds, processes for the preparation thereof, and a pharmaceutical composition containing the same. More particularly, it relates to 3-aminocarbonyl-1,4-dihydropyridine-5-carboxylic acid compounds of the formula:

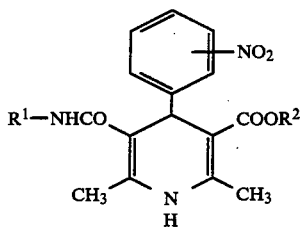

[I]

wherein $R^1$ is hydrogen atom, an alkyl having 1 to 5 carbon atoms, an alkenyl having 2 to 5 carbon atoms, an alkynyl having 3 to 5 carbon atoms, or a cycloalkyl having 3 to 8 carbon atoms, $R^2$ is an alkyl having 1 to 10 carbon atoms, and the $NO_2$ group is substituted at ortho- or meta-position, provided that when the $NO_2$ group is substituted at ortho-position and $R^2$ is methyl, $R^1$ is an alkyl having 3 to 5 carbon atoms, an alkenyl having 2 to 5 carbon atoms, an alkynyl having 3 to 5 carbon atoms, or a cycloalkyl having 3 to 8 carbon atoms, and when the $NO_2$ group is substituted at meta-position and $R^1$ is hydrogen atom, $R^2$ is an alkyl having 3 to 10 carbon atoms, and processes for the preparation thereof, and a pharmaceutical composition containing as an active ingredient the compound (I), which is particularly suitable for the prophylaxis and treatment of circulatory diseases.

Prior Art

A plenty of investigation have hitherto been done as to 1,4-dihydropyridine derivatives, particularly their 3,5-dicarboxylic acid esters, and some compounds are known to exhibit interesting coronary vasodilatory activity and hypotensive activity. For example, nifedipine [chemical name: dimethyl 1,4-dihydro-2,6-dimethyl-4-(2-nitophenyl)3,5-pyridinedicarboxylate] (Compound A) is widely used as a medicine for the prophylaxis and treatment of angina pectoris, and nicardipine [chemical name: methyl, N-benzyl-N-methylaminoethyl 1,4-dihydro-2,6-dimethyl-4-(3-nitrophenyl)-3,5-pyridinedicarboxylate hydrochloride] (Compound B) is widely used as a hypotensive or cerebral vasodiltory agent. Moreover, some 1,4-dihydropyridine-3,5-asymetic dicarboxylic acid esters are disclosed in Japanese Patent Second Publication (Kokoku) No. 29989/1980 and Japanese Patent First Publication (Kokai) Nos. 146565/1983 and 7255/1986.

Besides, there are known some compounds analogous to the compounds of this invention, for example, 3-aminocarbonyl-1,4-dihydropyridiene-5-carboxylic acid compounds in German Patent First Publication (Offenlegungsschrift) No. 2,228,377, Japanese Patent Second Publication (Kokoku) No. 20953/1982, and Japanese Patent First Publication (Kokai) No. 116267/1984, and 1,4-dihydropyridine-3-nitro-5-carboxylic cycloalkylamide in Japanese Patent First Publication (Kokai) No 227860/1984. Among theses, the following compounds have a chemical structure most similar to that of the compounds of this invention.

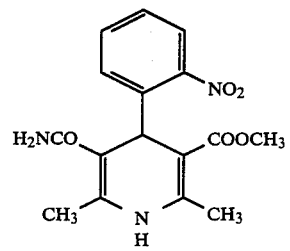

(Compound C)

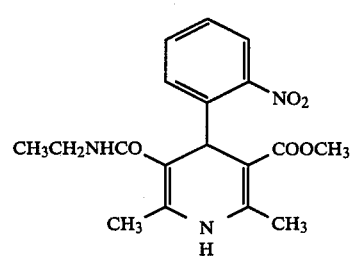

(Compound D)

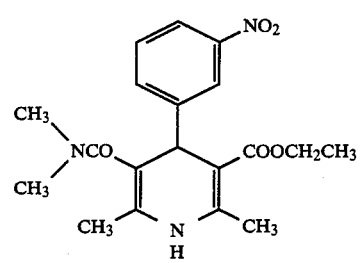

(Compound E)

These compounds are different from the compounds of this invention in the amido substituent and alkyl ester groups, and these literatures disclose insufficiently the pharmacological activities thereof.

BRIEF SUMMARY OF THE INVENTION

An object of the invention is to provide novel 3-aminocarbonyl-1,4-dihydropyridine-5-carboxylic acid compounds of the formula [I] which have excellent pharmacological activities. Another object of the invention is to provide novel compounds [I] as set forth above which are suitable for prophylaxis and treatment of circulator diseases, particularly hypertension and angina pectoris. A further object of the invention is to provide processes for preparing these compounds. Still further object of the invention is to provide a pharmaceutical composition containing as an active ingredient the compound [I]. These and other objects and advantages of the invention will be apparent to skilled persons from the following description.

DETAILED DESCRIPTION OF THE INVENTION

The novel 3-aminocarbonyl-1,4-dihydropyridine-5carboxylic acid compounds of the invention have the formula [I] as disclosed hereinbefore.

The alkyl for R[1] in the formula [I] denotes a straight or branched chain alkyl group having 1 to 5 carbon atoms, such as methyl, ethyl, n-propyl, isopropyl, n-butyl, isobutyl, sec-butyl, tert-butyl, n-pentyl, isopentyl, etc., preferably an alkyl having 3 to 5 carbon atoms, particularly preferably isopropyl. The alkenyl for R[1] denotes an alkenyl group having 2 to 5 carbon atoms, such as vinyl, allyl, 2-butenyl, 2-pentenyl, etc., particularly preferably allyl. The alkynyl denotes an alkynyl group having 3 to 5 carbon atoms, such as propargyl, 2-butyn-1-yl, etc., particularly preferably propargyl. The alkyl for R[2] denotes a straight or branched chain alkyl group having 1 to 10 carbon atoms, such as methyl, ethyl, n-propyl, isopropyl, n-butyl, isobutyl, sec-butyl, tert-butyl, 3-methyl-2-butyl, n-pentyl, isopentyl, 2-pentyl, 3-pentyl, tert-pentyl, n-hexyl, isohexyl, n-heptyl, n-octyl, n-nonyl, n-decyl, etc., preferably an alkyl having 1 to 9 carbon atoms, more preferably an alkyl having 1 to 3 or 6 to 9 carbon atoms, particularly preferably n-hexyl, n-heptyl, n-octyl, and n-nonyl. The $NO_2$ group is substituted at ortho (o) or meta (m) position, preferably o-position.

The compounds of this invention can be prepared by various processes, for example by the following processes.

[Process A]:
Reaction Scheme-1

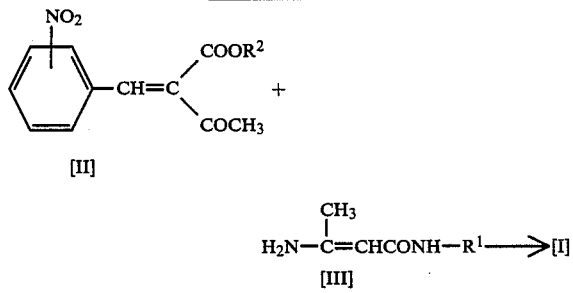

wherein the substitution position of $NO_2$, R[1] and R[2] are as defined above.

As is shown in the above Reaction Scheme-1, an alkyl o-(or m-)nitrobenzylideneacetoacetate [II] and a 3aminocrotonamide [III] are subjected to a cyclization reaction in an appropriate solvent to give the desired compound [I].

This reaction is usually carried out at a temperature of from room temperature to about 160° C., preferably about 50° to 130° C., more particularly at a boiling temperature of an appropriate inert solvent. The solvent includes, for example, aromatic hydrocarbons (e.g. benzene, toluene, xylene), alcohols (e.g. methanol, ethanol, propanol, isopropanyl, n-butanol, sec-butanol, etc.), ethers (e.g. diethyl ether, dioxane, tetrahydrofuran, ethylene glycol monomethyl ether, ethylene glycol dimethyl ether, etc.), acetic acid, pyridine, N,N-dimethylformamide, dimethylsulfoxide, acetonitrile, and the like. The reaction is preferably carried out while removing the produced water by azeotropic distillation using a non-polar solvent (e.g. benzene, toluene, xylene, etc.). In this case, the reaction is completed when a stoichiometric amount of water is distilled out. By this process, the desired compound [I] can be obtained in higher yield with less by-product in comparison with a process using other solvent.

The above reaction is usually completed in a period of 1 to 7 hours. The amount of the starting compounds is in the range of [II]:[III]=1:1.5 mole to 1.5:1 mole.

The starting compound [II] is known or can be prepared by a known process as shown in the following Reaction Scheme-2 [cf. Organic Reactions, 15, 204–599 (1967)].

Reaction Scheme-2

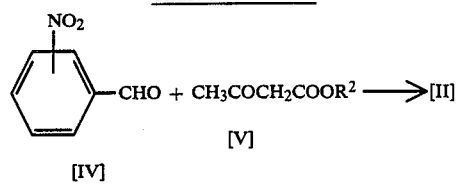

wherein the substitution position of $NO_2$ group and R[2] are as defined above.

That is, a nitrobenzaldehyde [IV] is reacted with an alkyl acetoacetate [V] in an appropriate solvent to give the compound [II]. This reaction can be carried out under the conditions similar to those in Reaction Scheme-1 by using similar solvent. The compound [II] may be used for the reaction with the compound [III] in the Reaction Scheme-1 after isolation from the reaction mixture or without isolation. The reactions of Reaction Schemes-1 and -2 may continuously be carried out in a single reaction system. That is, when the nitrobenzaldehyde [IV], alkyl acetoacetate [V] and 3-aminocrotonamide [III] are reacted under the same conditions as in Reaction Scheme-1, the desired compound [I] can directly be obtained. In this case, the starting compounds are used in the ratio of [IV]:[V]:[III]=1–1.5 mole:1–1.5 mole:1–1.5 mole.

The starting nitrobenzaldehyde [IV] used in Reaction Scheme-2 is known and the other starting alkyl acetoacetate [V] is also known or can be prepared by a known process, for example, by the process as shown in the following Reaction Scheme-3 (cf. U.S. Pat. No. 2,351,366).

Reaction Scheme-3

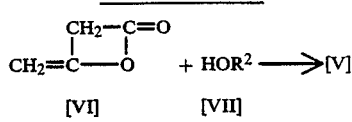

wherein R[2] is as defined above.

That is, a diketene [VI] is reacted with an alcohol [VII] in the presence of a basic catalyst in an inert solvent or without using any solvent at a temperature of about 40° to 130° C. to give the desired compound [V].

The other starting 3-aminocrotonamide [III] used in the above Reaction Scheme-1 is also known or can be prepared by a known process as shown in the following Reaction Scheme-4 [cf. J. Am. Chem. Soc., 67, 1017 (1945)].

Reaction Scheme-4

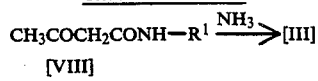

wherein R[1] is as defined above.

That is, an acetoacetamide [VIII] is dissolved in an appropriate solvent (e.g. methanol, ethanol, diethyl ether, dioxane, tetrahydrofuran, etc.) and thereto is blown an excess amount of ammonia gas at about 0° to 60° C. or is added a solution of ammonia in the above mentioned solvent, and the mixture is reacted in a sealed reactor at about 0° to 60° C. to give the desired compound [III].

[Process B]:
Reaction Scheme-5

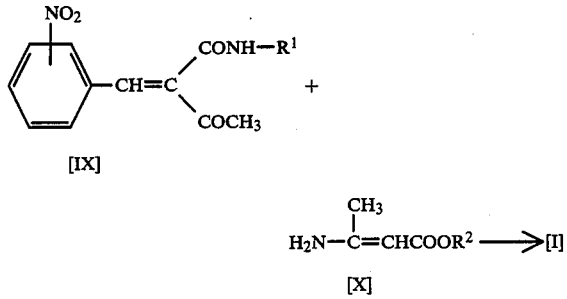

wherein the substitution position of $NO_2$, $R^1$ and $R^2$ are as defined above.

The compounds [I] of this invention can also be prepared by the process as shown in the above Reaction Scheme-5. That is, an o-(or m-)nitrobenzylideneacetoacetamide [IX] and an alkyl 3-aminocrotonate [X] are subjected to cyclization reaction in an appropriate solvent to give the desired compound [I]. This reaction can be done under substantially the same conditions as those in Reaction Scheme-1.

The starting compound [IX] is known or can be prepared by a known process as shown in the following Reaction Scheme-6 [Organic Reactions, 15, 204–599 (1967)].

Reaction Scheme-6

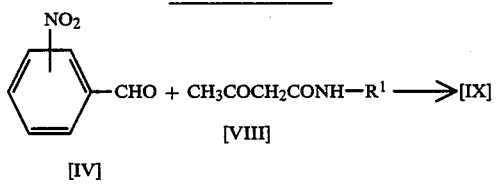

wherein the substitution position of $NO_2$ and $R^1$ are as defined above.

That is, a nitrobenzaldehyde [IV] is reacted with an acetoacetamide [VIII] in an appropriate solvent to give the compound [IX]. This reaction can be carried out under the same conditions using the same solvent as those in the above Reaction Scheme-5. The product [IX] obtained in this reaction can be used to the reaction with the compound [X] in the above Reaction Scheme-5 after being isolated from the reaction mixture or without isolation. Thus, the reactions of Reaction Scheme-5 and Reaction Scheme-6 may continuously be carried out in a single reaction system. That is, when the nitrobenzaldehyde [IV], alkyl acetoacetamide [VIII] and alkyl 3-aminocrotonate [X] are reacted under the same conditions as in Reaction Scheme-5, the desired compound [I] can directly be obtained. In this case, the starting compounds are used in the ratio of [IV]:-[VIII]:[X]=1–1.5 mole:1–1.5 mole:1–1.5 mole.

The starting acetoacetamide [VIII] used in Reaction Scheme-6 is also known or can be prepared by a known process, for example, by the process as shown in the following Reaction Scheme-7 (cf. German Pat. No. 1,142,859).

Reacton Scheme-7

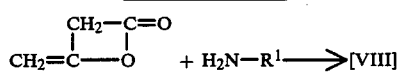

wherein $R^1$ is as defined above.

That is, a diketene [VI] is reacted with an amine [XI] in an inert solvent at a temperature of about −10° to 30° C. to give the desired compound [VIII].

The other starting alkyl 3-aminocrotonate [X] used in the above Reaction Scheme-5 is also known or can be prepared by a known process as shown in the following Reaction Scheme-8 [cf. J. Am. Chem. Soc., 67, 1017 (1945)].

Reaction Scheme-8

wherein $R^2$ is as defined above.

The reaction can be carried out under substantially the same conditions as those in the process of Reaction Scheme-4.

The compounds [I] obtained by the above processes can be isolated and purified from the reaction mixture by conventional isolation and purification methods, such as concentration, extraction, chromatography, re-precipitation, recrystallization, and the like.

The compounds of this invention have excellent pharmacological activities, for example, hypotensive, peripheral vasodilatory, coronary vasodilatory, cerebral vasodilatory and kidney vasodilatory activities, which activities are exhibited in mild with long lasting. Particularly, in comparison with the known 1,4-dihydropyridine derivatives (e.g. nifedipine, nicardipine hydrochloride), higher activities are exhibited in more mild with longer lasting. In view of the excellent properties which are not shown by the known compounds, the compounds of this invention are particularly useful. For instance, in case of the prophylaxis and treatment of hypertension, the compounds of this invention can exhibit stable hypotensive activity with less administration times (e.g. once or twice per day). Accordingly, the compounds of this invention are useful, for example, for the prophylaxis and treatment of hypertension, ischemic heart diseases (e.g. angina pectoris, myocardial infarction, etc.), and cerebral and peripheral circulation diseases.

The compounds of this invention can be used as a medicament in the form of a conventional pharmaceutical preparation in admixture with conventional pharmaceutically acceptable carriers, excipients and diluents. The pharmaceutical preparations include solid preparations such as powders, granules, fine granules, tablets, capsules, suppositories, and liquid preprations such as solutions, suspensions, emulsions, injections, and the like. These preparations are administered in oral route or in parenteral route. The dose of the compounds of this invention may vary according to the administration routes, severity of the disease, the sex, age and weight of the patient, but is usually in the range of 0.5 to 500 mg/day, preferably 1.0 to 150 mg/day, in case of adult patient suffering from hypertension, which may be divided one to several times per day.

The present invention is illustrated by the following Preparations, Examples and Experiments. In the Preparations and Examples, the melting point (no correction) of the compounds is measured by a heat plate method (using MP-S 2 type heat plate, manufactured by Yanagimoto, Japan).

Preparation 1

Preparation of methyl o-nitrobenzylideneacetoacetate:

o-Nitrobenzaldehyde (7.6 g, 0.05 mole) and methyl acetoacetate (5.8 g, 0.05 mole) are dissolved in benzene (40 ml), and thereto are added piperidine (0.2 ml) and acetic acid (0.6 ml), and the mixture is refluxed for 5 hours. The produced water is removed, and when a stoichiometic amount of water is distilled off, the reaction is stopped. After completion of the reaction, the reaction mixture is washed with 5% hydrochloric acid and then with water, and the solvent is distilled off under reduced pressure to give the title compound (12.2 g, yield 98%) as a brown oil.

Preparation 2

Preparation of 3-aminocrotonic methylamide:

N-methyl-acetoacetamide (175.4 g, 1.58 mole) is dissolved in ethanol (55 ml) and thereto is passed ammonia gas, wherein the temperature is controlled below 30° C. by cooling with water bath. After passing ammonia gas for about 3 hours, yellow crystals are precipitated. The mixture is allowed to stand at 0° C. for overnight. The resulting precipitates are washed with diethyl ether to give the title compound (115.2 g, yield 66%) as colorless prisms, m.p. 102° to 107° C.

In the same manner as described above, various compounds as shown in Table 1 are prepared.

TABLE 1

$$H_2N-\underset{\underset{CH_3}{|}}{C}=CHCONH-R^1$$

| Prepr. No. | $R^1$ | Melting point (°C.) | Yield (%) |
|---|---|---|---|
| 3 | H | 99–100 | 94.3 |
| 4 | $C_2H_5$ | 130–135 | 74.9 |
| 5 | $n-C_3H_7$ | 120–124 | 62.7 |
| 6 | $iso-C_3H_7$ | 143–145 | 54.6 |
| 7 | $n-C_4H_9$ | Semi-solid | 91.2 |
| 8 | $iso-C_4H_9$ | Oil | 98.0 |
| 9 | $sec-C_4H_9$ | Semi-solid | 73.0 |
| 10 | $tert-C_4H_9$ | Oil | 98.0 |
| 11 | $n-C_5H_{11}$ | Oil | 88.6 |
| 12 | $iso-C_5H_{11}$ | Oil | 87.5 |

Preparation 13

Preparation of o-nitrobenzylideneacetoacetic isopropylamide:

o-Nitrobenzaldehyde (43.4 g, 0.29 mole) and acetoacetic isopropylamide (40.0 g, 0.29 mole) are dissolved in benzene (150 ml) and thereto are added piperidine (1.15 ml) and acetic acid (3.45 ml), and the mixture is refluxed and the produced water is removed. After the stoichiometic amount of water is distilled off, the reaction is stopped. After the reaction, the solvent is distilled off under reduced pressure, and the residue is recrystallized from ethanol to give the title compound (62.7 g, yield 78.4%) as colorless prisms, m.p. 132°–135° C.

IR (KBr, $cm^{-1}$): 1690, 1630, 1510, 1340

NMR (CDCl$_3$, δ: ppm): 0.91 (6H, d), 2.44 (3H, s), 3.60–4.20 (1H, m), 5.90–6.45 (1H, bd.), 7.15–8.25 (4H, m), 7.78 (1H, s)

Elementary analysis for $C_{14}H_{16}N_2O_4$: Calcd. (%): C,60.86: H,5.84: N,10.14 Found (%): C,60.64: H,5.89; N,10.01

Preparation 14

Preparation of 3-aminocrotonic allylamide:

Acetoacetic allylamide (111.4 g, 0.79 mole) is dissolved in ethanol (80 ml) and thereto is passed ammonia gas, while the temperature is controlled below 30° C. by cooling with a water bath. After passing ammonia gas for about 3 hours, colorless crystals precipitate. The reaction mixture is allowed to stand at 0° C. overnight. The precipitates are separated by filtration and washed with diethyl ether to give the title compound (91.5 g, yield 82.7%) as colorless prisms, m.p. 143°–144° C.

Elementary analysis for $C_7H_{12}N_2O$: Calcd. (%): C,59.97: H,8.63: N,19.99 Found (%): C,59.78: H,8.76; N,20.08

Preparation 15

Preparation of 3-aminocrotonic propargylamide:

Acetoacetic propargylamide (93.4 g, 0.67 mole) is dissolved in ethanol (70 ml) and thereto is passed ammonia gas, while the temperature is controlled below 30° C. by cooling with a water bath. After passing ammonia gas for about 3 hours, colorless crystals precipitate. The reaction mixture is allowed to stand at 0° C. overnight. The precipitates are separated by filtration and washed with diethyl ether to give the title compound (87.7 g, yield 94.6%) as colorless needles, m.p. 137°–138° C.

Elementary analysis for $C_7H_{10}N_2O$: Calcd. (%): C,60.85: H,7.30; N,20.28 Found (%): C,60.80; H,7.34: N,20.56

Preparation 16

Preparation of o-nitrobenzylideneacetoacetic allylamide:

o-Nitrobenzaldehyde (7.6 g, 0.05 mole) and acetoacetic allylamide (7.1 g, 0.05 mole) are dissolved in benzene (40 ml) and thereto are added piperidine (0.2 ml) and acetic acid (0.6 ml), and the mixture is refluxed for 2 hours and the produced water is removed. After the stoichiometric amount of water is distilled off, the reaction is stopped. After the reaction, the reaction mixture is washed with 5% hydrochloric acid and then with water, and the solvent is distilled off under reduced pressure, and to the residue is added diethyl ether, and the obtained crude crystals are recrystallized from ethanol to give the title compound (9.6 g, yield 69.7%) as colorless needles, m.p. 128°–129° C.

Elementary analysis for $C_{14}H_{14}N_2O_4$: Calcd. (%): C,61.31; H,5.15; N,10.21 Found (%): C,61.38: H,5.13: N,10.10

Preparation 17

Preparation of o-nitrobenzylideneacetoacetic propargylamide:

o-Nitrobenzaldehyde (7.6 g, 0.05 mole) and acetoacetic propargylamide (7.0 g, 0.05 mole) are dissolved in benzene (40 ml) and thereto are added piperidine (0.2 ml) and acetic acid (0.6 ml), and the mixture is refluxed for 2 hours and the produced water is removed. After the stoichiometic amount of water is distilled off, the reaction is stopped. After the reaction, the reaction mixture is washed with 5% hydrochloric acid and then with water, and the solvent is distilled off under reduced pressure, and to the residue is added diethyl ether, and the obtained crude crystals are recrystallized from ethanol to give the title compound (10.9 g, yield 80.2%) as colorless needles, m.p. 136°–137° C.

Elementary analysis for $C_{14}H_{12}N_2O_4$: Calcd. (%): C,61.76: H,4.44: N,10.29 Found (%): C,61.64; H,4.43: N,10.26

Preparation of 18

Preparation of acetoacetic cyclopropylamide:

Cyclopropylamine (42.2 g, 0.74 mole) is dissolved in chloroform (300 ml) and thereto is added dropwise diketene (62.1 g, 0.74 mole) over a period of 1–1.5 hour with stirring in an ice bath. After the addition, the mixture is stirred at 40° C. for one hour, and the solvent is distilled off under reduced pressure, and the residue is recrystallized from benzene-n-hexane to give the title compound (83.4 g, yield 80%) as colorless needles, m.p. 65°–66° C.

Elementary analysis for $C_7H_{11}NO_2$ Calcd. (%): C,59.55: H,7.85: N,9.92 Found (%): C,59.37: H,7.99; N,9.68

Preparation 19

Preparation of 3-aminocrotonic cyclopropylamide:

Acetoacetic cyclopropylamide (209.4 g, 1.48 mole) is dissolved in ethanol (160 ml) and thereto is passed ammonia gas, while the temperature is controlled below 30° C. by cooling with a water bath. After passing ammonia gas for about 3 hours, yellow crystals precipitate. The reaction mixture is allowed to stand at 0° C. overnight. The precipitates are separated by filtration and washed with diethyl
(172.2 g, yield 82.8%) as colorless prisms, m.p. 169°–171° C.

Elementary analysis for $C_7H_{12}N_2O$: Calcd. (%): C,59.97: H,8.63: N,19.99 Found (%): C,59.71: H,8.77: N,20.17

Preparation 20

Preparation of 3-aminocrotonic cyclopentylamide:

Acetoacetic cyclopentylamide (169.1 g, 1.00 mole) is dissolved in ethanol (100 ml) and thereto is passed ammonia gas, while the temperature is controlled below 30° C. by cooling with a water bath. After passing ammonia gas for about 3 hours, colorless crystals precipitate. The reaction mixture is allowed to stand at 0° C. overnight. The precipitates are separated by filtration and washed with diethyl ether to give the title compound (140.4 g, yield 85.6%) as colorless needles, m.p. 138°–139° C.

Elementary analysis for $C_9H_{16}N\ N_2O$: Calcd. (%): C,64.25: H,9.59: N,16.65 Found (%): C,64.03: H,9.79; N,16.53

Preparation 21

Preparation of o-nitrobenzylideneacetoacetic cyclopropylamide:

o-Nitrobenzaldehyde (7.6 g, 0.05 mole) and acetoacetic cyclopropylamide (7.1 g, 0.05 mole) are dissolved in benzene (40 ml) and thereto are added piperidine (0.2 ml) and acetic acid (0.6 ml), and the mixture is refluxed for 2 hours and the produced water is removed. After the stoichiometic amount of water is distilled off, the reaction is stopped. After the reaction, the reaction mixture is washed with 5% hydrochloric acid and then with water, and the solvent is distilled off under reduced pressure, and to the residue is added diethyl ether, and the obtained crude crystals are recrystallized from ethanol to give the title compound (10.4 g, yield 75.6%) as colorless needles, m.p. 133°–134° C.

Elementary analysis for $C_{14}H_{14}N_2O_4$: Calcd. (%): C,61.31: H,5.15: N,10.21 Found (%): C,61.55: H,5.20: N,10.12

Preparation 22

Preparation of o-nitrobenzylideneacetoacetric cyclopentylamide:

o-Nitrobenzaldehyde (7.6 g, 0.05 mole) and acetoacetic cyclopentylamide (8.5 g, 0.05 mole) are dissolved in benzene (40 ml) and thereto are added piperidine (0.2 ml) and acetic acid (0.6 ml), and the mixture is refluxed for 2 hours and the produced water is removed. After the stoichiometic amount of water is distilled off, the reaction is stopped. After the reaction, the reaction mixture is washed with 5% hydrochloric acid and then with water, and the solvent is distilled off under reduced pressure, and to the residue is added diethyl ether, and the obtained crude crystals are recrystallized from ethanol to give the title compound (10.6 g, yield 70.2%) as colorless prisms, m.p. 132°–134° C.

Elementary analysis for $C_{16}H_{18}N_2O_4$: Calcd. (%): C,63.56: H,6.00; N,9.27 Found (%): C,63.40; H,6.13: N,9.35

EXAMPLE 1

Preparation of n-heptyl 2,6-dimethyl-3-isopropylaminocarbonyl-4-(o-nitrophenyl)-1,4-dihydropyridine-5-carboxylate:

n-Heptyl o-nitrobenzylideneacetoacetate (16.7 g, 0.05 mole) and 3-aminocrotonic isopropylamide (7.1 g, 0.05 mole) are dissolved in benzene (100 ml), and the mixture is refluxed for 7 hours. The produced water is removed by azeotropic distillation. After the stoichiometric amount of water is removed, which is measured by taking the water with a moisture meter, the reaction is stopped.

After completion of the reaction, the solvent is distilled off under reduced pressure. To the residue is added diethyl ether, and the precipitated crystals are separated by filtration and recrystallized from 80% ethanol to give the title compound (15.7 g, yield 68.6%) as yellow prisms, m.p. 137°–139° C.

IR (KBr, $cm^{-1}$): 1680, 1525, 1355

NMR (DMSO, δ: ppm): 0.70–1.30 (13H, m), 0.85–1.10 (6H, d.d), 2.00 (3H, s), 2.20 (3H, s), 3.50–4.00 (3H, m), 5.25 (1H, s), 7.00–7.65 (4H, m), 7.08 (1H, d), 8.20 (1H, s)

Elementary analysis for $C_{25}H_{35}N_3O_5$: Calcd. (%): C,65.62; H,7.71: N,9.18 Found (%): C,65.90: H,7.67: N,9.46

EXAMPLE 2

Preparation of n-octyl 2,6-dimethyl-3-isopropylaminocarbonyl-4-(o-nitrophenyl)-1,4-dihydropyridine-5-carboxylate:

n-Octyl o-nitrobenzylideneacetoacetate (17.4 g, 0.05 mole) and 3-aminocrotonic isopropylamide (7.1 g, 0.05 mole) are dissolved in benzene (100 ml), and the mixture is refluxed for 7 hours. The produced water is removed by azeotropic distillation. After the stoichiometric amount of water is removed, which is measured by taking the water with a moisture meter, the reaction is stopped.

After completion of the reaction, the solvent is distilled off under reduced pressure. To the residue is added diethyl ether, and the precipitated crystals are separated by filtration and recrystallized from 80% ethanol to give the title compound (13.8 g, yield 58.4%) as yellow prisms, m.p. 126°–129° C.

IR (KBr, cm$^{-1}$): 1685, 1525, 1355

NMR (DMSO, δ: ppm): 0.80–1.50 (15H, m), 0.85–1.10 (6H, d.d), 2.00 (3H, s), 2.20 (3H, s), 3.50–4.00 (3H, m), 5.25 (1H, s), 7.00–7.65 (4H, m), 7.10 (1H, d), 8.25 (1H, s)

Elementary analysis for $C_{26}H_{37}N_3O_5$: Calcd. (%): C,66.22: H,7.91: N,8.91 Found (%): C,66.15: H,7.80: N,8.82

EXAMPLE 3

Preparation of n-nonyl 2,6-dimethyl-3-isopropylaminocarbonyl-4-(o-nitrophenyl)-1,4-dihydropyridine-5-carboxylate:

n-Nonyl o-nitrobenzylideneacetoacetate (18.1 g, 0.05 mole) and 3-aminocrotonic isopropylamide (7.1 g, 0.05 mole) are dissolved in benzene (100 ml), and the mixture is refluxed for 7 hours. The produced water is removed by azeotropic distillation. After the stoichiometric amount of water is removed, which is measured by taking the water with a moisture meter, the reaction is stopped.

After completion of the reaction, the solvent is distilled off under reduced pressure. To the residue is added diethyl ether, and the precipitated crystals are separated by filtration and recrystallized from 80% ethanol to give the title compound (14.6 g, yield 60.3%) as yellow prisms, m.p. 147°–149° C.

IR (KBr, cm$^{-1}$): 1685, 1525, 1355

NMR (DMSO, δ: ppm): 0.80–1.50 (17H, m), 0.85–1.10 (6H, d.d), 2.00 (3H, s), 2.20 (3H, s), 3.50–4.00 (3H, m), 5.30 (1H, s), 7.00–7.65 (4H, m), 7.14 (1H, d), 8.25 (1H, s)

Elementary analysis for $C_{27}H_{95}N_3O_5$: Calcd. (%): C,66.78: H,8.10: N,8.65 Found (%): C,66.73: H,7.97: N,8.48

EXAMPLE 4

Preparation of n-hexyl 2,6-dimethyl-3-aminocarbonyl-4-(o-nitrophenyl)-1,4-dihydropyridine-5carboxylate:

n-Hexyl o-nitrobenzylideneacetoacetate (16.0 g, 0.05 mole) and 3-aminocrotonamide (5.0 g, 0.05 mole) are dissolved in ethanol (100 ml), and the mixture is refluxed for 8 hours. After the reaction, the solvent is distilled off under reduced pressure. The residue is dissolved in eluting solvent [chloroform:carbon tetrachloride:ethyl formate:formic acid:ethanol (10:10:8:1:2)] (30 ml) and subjected to column chromatography [silica gel 60 Art. 9385 (Manufactured by Merck Co.), 600 g, ϕ40 mm×1 m]. The fraction containing the desired compound is regulated to pH 10 with 28% aqueous ammonia, and the organic layer is separated, washed with water, dried over anhydrous magnesium sulfate and then concentrated under reduced pressure. The residue is recrystallized from ethanol to give the title compound (17.1 g, yield 80.6%) as yellow prisms, m.p. 120°–123° C.

IR (KBr, cm$^{-1}$): 1680, 1520, 1350

NMR (DMSO, δ: ppm): 0.50–1.50 (11H, m), 2.10 (3H, s), 2.20 (3H, s), 3.50–4.00 (3H, m), 5.32 (1H, s), 6.75 (2H, s), 7.00–7.70 (4H, m), 8.35 (1H, s)

Elementary analysis for $C_{21}H_{27}N_3O_5 \cdot \frac{1}{2}C_2H_5OH$: Calcd. (%): C,62.25; H,7.12: N,9.90 Found (%): C,62.36; H,7.14: N,9.98

EXAMPLE 5

Preparation of methyl 2,6-dimethyl-3-isopropylaminocarbonyl-4-(o-nitrophenyl)-1,4-dihydropyridine-5-carboxylate:

o-Nitrobenzylideneacetoacetic isopropylamide (4.5 g, 0.016 mole) and methyl 3-aminocrotonate (2.0 g, 0.016 mole) are dissolved in ethanol (10 ml), and the mixture is refluxed for 14 hours. After the reaction, the solvent is distilled off under reduced pressure. The residue is dissolved in elution solvent [chloroform:carbon tetrachloride:ethyl formate:formic acid:ethanol (10:10:8:1:2)] (30 ml) and subjected to column chromatography [silica gel 60 Art. 9385 (Manufactured by Merck Co.), 300 g, ϕ40 mm×50 cm]. The fraction containing the desired compound is regulated to pH 10 with 28% aqueous ammonia, and the organic layer is separated, washed with water, dried over anhydrous magnesium sulfate and then concentrated under reduced pressure. The residue is recrystallized from ethanol to give the title compound (3.6 g, yield 57.0%) as yellow prisms, m.p. 203°–206° C.

IR (KBr, cm$^{-1}$): 1680, 1525, 1360

NMR (DMSO, ppm): 0.90–1.20 (6H, d.d), 2.10 (3H, s), 3.45 (3H, s), 3.60–4.10 (1H, m), 5.32 (1H, s), 7.30–7.90 (5H, m), 8.55 (1H, s)

Elementary analysis for $C_{19}H_{23}N_3O_5$: Calcd. (%): C,61.11: H,6.21: N,11.25 Found (%): C,60.84; H,5.99; N,11.32

EXAMPLE 6

Preparation of n-butyl 2,6-dimethyl-3-isopropylaminocarbonyl-4-(o-nitrophenyl)-1,4-dihydropyridine-5-carboxylate:

o-nitrobenzylideneacetoacetic isopropylamide (13.8 g, 0.05 mole) and n-butyl 3-aminocrotonate (7.9 g, 0.05 mole) are dissolved in benzene (100 ml), and the mixture is refluxed for 5 hours. The produced water is removed by azeotropic distillation. After the stoichiometric amount of water is removed, which is measured by taking the water with a moisture meter, the reaction is stopped.

After completion of the reaction, the solvent is distilled off under reduced pressure. To the residue is added diethyl ether, and the precipitated crystals are separated by filtration and recrystallized from 80% ethanol to give the title compound (8.3 g, yield 40.0%) as yellow prisms, m.p. 194°–196° C.

IR (KBr, cm$^{-1}$): 1675, 1525, 1355

NMR (DMSO, δ: ppm): 0.70–1.20 (6H, m), 0.70–1.70 (7H, m), 2.10 (3H, s), 2.30 (3H, s), 3.50–4.10 (3H, m), 5.50 (1H, s), 7.30–7.95 (4H, m), 7.42 (1H, d), 8.55 (1H, s)

Elementary analysis for $C_{22}H_{29}N_3O_5$: Calcd. (%): C,63.59: H,7.04: N,10.11 Found (%): C,63.76: H,6.82: N, 9.84

EXAMPLE 7

Preparation of n-hexyl 2,6-dimethyl-3-isopropylaminocarbonyl-4-(o-nitrophenyl)-1,4-dihydropyridine-5-carboxylate:

o-Nitrobenzaldehyde (3.8 g, 0.025 mole), n-hexyl acetoacetate (4.6 g, 0.025 mole) and 3-aminocrotonic isopropylamide (3.5 g, 0.025 mole) are dissolved in ethanol (50 ml), and the mixture is refluxed for 8 hours. After the reaction, the solvent is distilled off under reduced pressure. The residue is dissolved in elution solvent [chloroform:carbon tetrachloride:ethyl formate:formic acid:ethanol (10:10:8:1:2)] (30 ml) and subjected to column chromatography [silica gel 60 Art. 9385 (Manufactured by Merck Co.), 300 g, φ40 mm×50 cm]. The fraction containing the desired compound is regulated to pH 10 with 28% aqueous ammonia, and the organic layer is separated, washed with water, dried over anhydrous magnesium sulfate and then concentrated under reduced pressure. The residue is recrystallized from 80% ethanol to give the title compound (3.31 g, yield 29.9%) as yellow prisms, m.p. 175°–178° C.

IR (KBr, cm$^{-1}$): 1675, 1525, 1360

NMR (DMSO, δ: ppm): 0.60–1.60 (9H, m), 0.80–1.10 (6H, d.d), 2.00 (3H, s), 2.20 (3H, s), 3.50–4.00 (3H, m), 5.30 (1H, s), 7.00–7.70 (4H, m), 7.15 (1H, d), 8.25 (1H, s)

Elementary analysis for $C_{24}H_{33}N_3O_5$: Calcd. (%): C,64.99: H,7.50: N,9.47 Found (%): C,65.20; H,7.59: N,9.47

EXAMPLE 8

Preparation of n-pentyl 2,6-dimethyl-3-isopropylaminocarbonyl-4-(o-nitrophenyl)-1,4-dihydropyridine-5-carboxylate:

o-Nitrobenzaldehyde (3.8 g, 0.025 mole), n-pentyl 3-aminocrotonate (4.3 g, 0.025 mole) and acetoacetic isopropylamide (3.6 g, 0.025 mole) are dissolved in ethanol (50 ml), and the mixture is refluxed for 8 hours. After the reaction, the solvent is distilled off under reduced pressure. The residue is dissolved in elution solvent [chloroform:carbon tetrachloride:ethyl formate:formic acid:ethanol (10:10:8:1:2)] (30 ml) and subjected to column chromatography [silica gel 60 Art. 9385 (Manufactured by Merck Co.), 300 g, φ40 mm×50 cm]. The fraction containing the desired compound is regulated to pH 10 with 28% aqueous ammonia, and the organic layer is separated, washed with water, dried over anhydrous magnesium sulfate and then concentrated under reduced pressure. The residue is recrystallized from 80% ethanol to give the title compound (3.2 g, yield 30.0%) as yellow prisms, m.p. 186°–189° C.

IR (KBr, cm$^{-1}$): 1680, 1525, 1360

NMR DMSO, δ: ppm): 0.60–1.20 (6H, m), 0.60–1.60 (9H, m), 2.00 (3H, s), 2.20 (3H, s), 3.50–4.00 (3H, m), 5.30 (1H, s), 7.00–7.70 (4H, m), 7.17 (1H, d), 8.30 (1H, s)

Elementary analysis for $C_{23}H_{31}N_3O_5$: Calcd. (%): C,64.31; H,7.28; N,9.78 Found (%): C,64.45; H,7.34; N,10.04

EXAMPLES 9 TO 70

In the same manner as described in Examples 1 to 8, the compounds are shown in Table 2 are prepared, wherein the compounds obtained in Examples 9 to 56 has the $NO_2$ group at ortho-position, and the compounds obtained in Examples 57 to has the $NO_2$ group at meta-position.

TABLE 2

| Ex. No. | R$^1$ | R$^2$ | M.p. (°C.) | Appearance (solvent for recrystallization) |
|---|---|---|---|---|
| 9 | H | —C$_2$H$_5$ | 209–211 | Yellow prisms (ethanol) |
| 10 | " | —C$_3$H$_7$(n) | 178–180 | " |
| 11 | " | —C$_3$H$_7$(iso) | 219–221 | " |
| 12 | " | —C$_4$H$_9$(n) | 100–103 | Yellow prisms (ethyl acetate) |
| 13 | " | —C$_4$H$_9$(iso) | 194–196 | " |
| 14 | " | —C$_4$H$_9$(sec) | 180–182 | " |
| 15 | " | —C$_4$H$_9$(tert) | 232–234 | Yellow prisms (ethanol) |
| 16 | " | —C$_5$H$_{11}$(n) | 112–115 | " |
| 17 | " | —C$_5$H$_{11}$(iso) | 163–165.5 | Yellow prisms (ethyl acetate) |
| 18 | " | 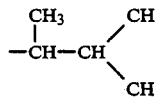 | 181–183 | Yellow prisms (ethanol) |
| 19 | H | —C$_5$H$_{11}$(sec) | 152–154 | Yellow prisms (ethyl acetate) |
| 20 | " | —C$_5$H$_{11}$(tert) | 187–189 | Yellow prisms (ethanol) |
| 21 | " | 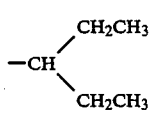 | 172–174 | Yellow prisms (ethyl acetate) |
| 22 | " | —C$_7$H$_{15}$(n) | 120–124 | Yellow prisms (ethanol) |

TABLE 2-continued

| Ex. No. | R¹ | R² | M.p. (°C.) | Appearance (solvent for recrystallization) |
|---|---|---|---|---|
| 23 | " | —C₈H₁₇(n) | 187–189 | " |
| 24 | —CH₃ | —C₂H₅ | 203–205 | " |
| 25 | " | —C₃H₇(n) | 203–204 | " |
| 26 | " | —C₄H₉(n) | 188–190 | Pale Yellow prisms (ethanol) |
| 27 | " | —C₅H₁₁(iso) | 212–214 | Yellow prisms (ethanol) |
| 28 | " | —C₆H₁₃(n) | 119–122 | Yellow prisms (ethyl acetate) |
| 29 | —C₂H₅ | —C₂H₅ | 182–185 | Yellow prisms (ethanol) |
| 30 | " | —C₃H₇(n) | 188–191 | " |
| 31 | " | —C₄H₉(n) | 171–173 | " |
| 32 | " | —C₅H₁₁(n) | 169–171 | Yellow prisms (ethanol + H₂O) |
| 33 | " | —C₅H₁₁(iso) | 154–157 | Yellow prisms (ethanol) |
| 34 | —C₂H₅ | —C₇H₁₅(n) | 86–88 | Yellow prisms [ethanol + iso-(C₃H₇)₂O] |
| 35 | —C₃H₇(n) | —CH₃ | 195–197 | Yellow prisms (ethanol) |
| 36 | " | —C₂H₅ | 154–156 | Orange prisms (ethanol) |
| 37 | " | —C₃H₇(n) | 150–152 | Pale yellow prisms (ethanol) |
| 38 | " | —C₄H₉(n) | 142–144 | Yellow prisms (ethanol) |
| 39 | " | —C₅H₁₁(n) | 156–158 | Yellow prisms (ethanol + H₂O) |
| 40 | " | —C₅H₁₁(iso) | 170–172 | Yellow prisms (ethanol) |
| 41 | " | —C₆H₁₃(n) | 157–160 | Yellow prisms (dil. ethanol) |
| 42 | " | —C₇H₁₅(n) | 130–132 | " |
| 43 | —C₃H₇(iso) | —C₂H₅ | 216–218 | Yellow prisms (ethanol) |
| 44 | " | —C₃H₇(n) | 150–152 | " |
| 45 | " | —C₃H₇(iso) | 182–185 | " |
| 46 | " | —C₄H₉(iso) | 196–199 | " |
| 47 | " | —C₅H₁₁(iso) | 197–199 | Pale yellow prisms (ethanol) |
| 48 | " | 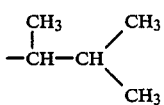 | 175–178 | Yellow prisms (dil. ethanol) |
| 49 | —C₃H₇(iso) | —C₅H₁₁(sec) | 180–182 | Orange prisms (dil. ethanol) |
| 50 | " | 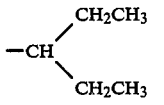 | 205–208 | Yellow prisms (dil. ethanol) |
| 51 | " | —C₆H₁₃(iso) | 175–177 | " |
| 52 | " | —C₁₀H₂₁(n) | 126–129 | " |
| 53 | —C₄H₉(n) | —C₅H₁₁(iso) | 152–158 | " |
| 54 | —C₄H₉(iso) | —C₅H₁₁(iso) | 175–178 | |
| 55 | —C₅H₁₁(n) | " | 130–132 | " |
| 56 | —C₅H₁₁(iso) | " | 166–169 | " |
| 57 | H | —C₃H₇(iso) | 188–190 | Yellow prisms (ethanol) |
| 58 | " | —C₄H₉(tert) | 178.5–179 | Yellow prisms (benzene + n-hexane) |
| 59 | —C₂H₅ | —C₄H₉(n) | 185–187 | Yellow prisms (ethanol + H₂O) |
| 60 | —C₃H₇(iso) | —CH₃ | 180–181 | " |
| 61 | " | —C₂H₅ | 193–195 | Pale yellow prisms (ethanol + H₂O) |
| 62 | " | —C₃H₇(n) | 213–214 | Yellow prisms (ethanol) |
| 63 | " | —C₃H₇(iso) | 193–194 | Yellow prisms (methanol) |

TABLE 2-continued

| Ex. No. | $R^1$ | $R^2$ | M.p. (°C.) | Appearance (solvent for re-crystallization) |
|---|---|---|---|---|
| 64 | —C$_3$H$_7$(iso) | —C$_4$H$_9$(n) | 200–202 | Yellow prisms (ethanol + H$_2$O) |
| 65 | " | —C$_4$H$_9$(iso) | 238–241 | Yellow prisms (Tetrahydrofuran + methanol) |
| 66 | " | —C$_5$H$_{11}$(n) | 190–193 | Yellow prisms (ethanol) |
| 67 | " | —C$_5$H$_{11}$(iso) | 198–201 | " |
| 68 | —C$_3$H$_7$(n) | —C$_4$H$_9$(n) | 155–157 | Yellow prisms (ethanol + H$_2$O) |
| 69 | —C$_4$H$_9$(n) | —C$_4$H$_9$(n) | 132–134 | " |
| 70 | —C$_4$H$_9$(iso) | " | 155–157 | " |

EXAMPLE 71

Preparation of methyl 2,6-dimethyl-3-allylaminocarbonyl-4-(o-nitrophenyl)-1,4-dihydrophridine-5-carboxylate:

Methyl o-nitrobenzylideneacetoacetate (12.5 g, 0.05 mole) and 3-aminocrotonic allylamide (7.0 g, 0.05 mole) are dissolved in benzene (60 ml), and the mixture is refluxed for 7 hours. The produced water is removed by azeotropic distillation. After the stoichiometric amount of water is removed, which is measured by taking the water with a moisture meter, the reaction is stopped.

After completion of the reaction, the solvent is distilled off under reduced pressure. To the residue is added diisopropyl ether, and the precipitated crystals are separated by filtration and recrystallized from 80% ethanol to give the title compound (15.7 g, yield 84.3%) as yellow prisms, m.p. 175°–177° C.

IR (KBr, cm$^{-1}$): 1680, 1525, 1355

NMR (DMSO, δ: ppm): 2.08 (3H, s), 2.20 (3H, s), 3.35 (3H, s), 3.50–3.85 (2H, m), 4.65–4.90 (1H, m), 5.00 (1H, s), 5.30 (1H, s), 5.40–6.00 (1H, m), 7.10–7.80 (5H, m), 8.45 (1H, s)

Elementary analysis for C$_{19}$H$_{21}$N$_3$O$_5$: Calcd. (%): C,61.44: H,5.70; N,11.32 Found (%): C,61.21: H,5.55: N,11.12

EXAMPLE 72

Preparation of n-hexyl 2,6-dimethyl-3-allylaminocarbonyl-4-(o-nitrophenyl)-1,4-dihydropyridine-5-carboxylate:

n-Hexyl o-nitrobenzylideneacetoacetate (16.0 g, 0.05 mole) and 3-aminocrotonic allylamide (7.0 g, 0.05 mole) are dissolved in benzene (60 ml), and the mixture is refluxed for 7 hours. The produced water is removed by azeotropic distillation. After the stoichiometric amount of water is removed, which is measured by taking the water with a moisture meter, the reaction is stopped.

After completion of the reaction, the solvent is distilled off under reduced pressure. To the residue is added diisopropyl ether, and the precipitated crystals are separated by filtration and recrystallized from 80% ethanol to give the title compound (14.2 g, yield 64.1%) as yellow prisms, m.p. 148°–150° C.

IR (KBr, cm$^{-1}$): 1680, 1525, 1360

NMR (DMSO, δ: ppm): 0.60–1.60 (11H, m), 2.05 (3H, s), 2.25 (3H, s), 3.50–4.00 (4H, m), 4.70–4.90 (1H, m), 5.00 (1H, s), 5.35 (1H, s), 5.50–6.00 (1H, m), 7.10–7.80 (4H, m), 8.40 (1H, s)

Elementary analysis for C$_{24}$H$_{31}$N$_3$O$_5$: Calcd. (%): C,65.28: H,7.08: N,9.52 Found (%): C,65.00: H,6.95; N,9.4

EXAMPLE 73

Preparation of n-heptyl 2,6-dimethyl-3-allylaminocarbonyl-4-(o-nitrophenyl)-1,4-dihydropyridine-5-carboxylate:

n-Heptyl o-nitrobenzylideneacetoacetate (16.7 g, 0.05 mole) and 3-aminocrotonic allylamide (7.0 g, 0.05 mole) are dissolved in benzene (60 ml), and the mixture is refluxed for 7 hours. The produced water is removed by azeotropic distillation. After the stoichiometric amount of water is removed, which is measured by taking the water with a moisture meter, the reaction is stopped.

After completion of the reaction, the solvent is distilled off under reduced pressure. To the residue is added diisopropyl ether, and the precipitated crystals are separated by filtration and recrystallized from 80% ethanol to give the title compound (14.1 g, yield 61.7%) as yellow prisms, m.p. 118°–120° C.

IR (KBr, cm$^{-1}$): 1680, 1525, 1360

NMR (DMSO, δ: ppm): 0.60–1.70 (13H, m), 2.05 (3H, s), 2.20 (3H, s), 3.50–4.00 (4H, m), 4.60–4.85 (1H, m), 4.95 (1H, s), 5.32 (1H, s), 5.40–6.00 (1H, m), 7.05–7.70 (5H, m), 8.33 (1H, s)

Elementary analysis for C$_{25}$H$_{33}$N$_3$O$_5$: Calcd. (%): C,65.91: H,7.30: N,9.23 Found (%) C,65.96: H,7.27: N,9.18

EXAMPLE 74

Preparation of n-octyl 2,6-dimethyl-3-allylaminocarbonyl-4-(o-nitrophenyl)-1,4-dihydropyridine-5-carboxylate:

n-Octyl o-nitrobenzylideneacetoacetate (17.4 g, 0.05 mole) and 3-aminocrotonic allylamide (7.0 g, 0.05 mole) are dissolved in benzene (60 ml), and the mixture is refluxed for 7 hours. The produced water is removed by azeotropic distillation. After the stoichiometric amount of water is removed, which is measured by taking the water with a moisture meter, the reaction is stopped.

After completion of the reaction, the solvent is distilled off under reduced pressure. To the residue is added diisopropyl ether, and the precipitated crystals are separated by filtration and recrystallized from 80% ethanol to give the title compound (12.3 g, yield 52.3%) as yellow prisms, m.p. 98°–100° C.

IR (KBr, cm$^{-1}$): 1690, 1520, 1355

NMR (DMSO, δ: ppm): 0.60–1.70 (15H, m), 2.05 (3H, s), 2.22 (3H, s), 3.50–4.00 (4H, m), 4.65–4.90 (1H, m), 5.00 (1H, s), 5.38 (1H, s), 5.50–6.00 (1H, m), 7.10–7.80 (5H, m), 8.42 (1H, s)

Elementary analysis for $C_{26}H_{35}N_3O_5$: Calcd. (%): C,66.50: H,7.51; N,8.95 Found (%): C,66.79: H,7.47: N,8.72

EXAMPLE 75

Preparation of n-nonyl 2,6-dimethyl-3-allylaminocarbonyl-4-(o-nitrophenyl)-1,4-dihydropyridine-5-carboxylate:

n-Nonyl o-nitrobenzylideneacetoacetate (18.1 g, 0.05 mole) and 3-aminocrotonic allylamide (7.0 g, 0.05 mole) are dissolved in benzene (60 ml), and the mixture is refluxed for 7 hours. The produced water is removed by azeotropic distillation. After the stoichiometric amount of water is removed, which is measured by taking the water with a moisture meter, the reaction is stopped.

After completion of the reaction, the solvent is distilled off under reduced pressure. To the residue is added diisopropyl ether, and the precipitated crystals are separated by filtration and recrystallized from 80% ethanol to give the title compound (12.3 g, yield 50.9%) as yellow prisms, m.p. 100°–102° C.

IR (KBr, cm$^{-1}$): 1675, 1525, 1360

NMR (DMSO, δ: ppm): 0.60–1.60 (17H, m), 2.05 (3H, s), 2.20 (3H, s), 3.40–4.00 (4H, m), 4.60–4.85 (1H, m), 4.95 (1H, s), 5.35 (1H, s), 5.40–6.00 (1H, m), 7.05–7.75 (5H, m), 8.38 (1H, s)

Elementary analysis for $C_{27}H_{37}N_3O_5$: Calcd. (%): C,67.05; H,7.71; N,8.69 Found (%): C,66.92: H,7.73: N,8.45

EXAMPLE 76

Preparation of methyl 2,6-dimethyl-3-propargylaminocarbonyl-4-(o-nitrophenyl)-1,4-dihydropyridine-5-carboxylate:

Methyl o-nitrobenzylideneacetoacetate (12.5 g, 0.05 mole) and 3-aminocrotonic propargylamide (6.9 g, 0.05 mole) are dissolved in benzene (60 ml), and the mixture is refluxed for 7 hours. The produced water is removed by azeotropic distillation. After the stoichiometric amount of water is removed, which is measured by taking the water with a moisture meter, the reaction is stopped.

After completion of the reaction, the solvent is distilled off under reduced pressure. To the residue is added diethyl ether, and the precipitated crystals are separated by filtration and recrystallized from 80% ethanol to give the title compound (15.3 g, yield 82.9%) as yellow prisms, m.p. 89°–91° C.

IR (KBr, cm$^{-1}$): 1710, 1515, 1355

NMR (DMSO, δ: ppm): 2.08 (3H, s), 2.19 (3H, s), 2.75–3.00 (1H, m), 3.33 (3H, s), 3.60 (2H, m), 5.25 (1H, s), 7.05–7.90 (5H, m), 8.45 (1H, s)

Elementary analysis for $C_{19}H_{19}N_3O_5 \cdot \frac{1}{4}C_2H_5OH$: Calcd. (%) C,61.49: H,5.42: N,11.03 Found (%): C,61.78: H,5.53: N,10.89

EXAMPLE 77

Preparation of n-heptyl 2,6-dimethyl-3-propargylaminocarbonyl-4-(o-nitrophenyl)-1,4-dihydropyridine-5-carboxylate:

n-Heptyl o-nitrobenzylideneacetoacetate (16.7 g, 0.05 mole) and 3-aminocrotonic propargylamide (6.9 g, 0.05 mole) are dissolved in benzene (60 ml), and the mixture is refluxed for 7 hours. The produced water is removed by azeotropic distillation. After the stoichiometric amount of water is removed, which is measured by taking the water with a moisture meter, the reaction is stopped.

After completion of the reaction, the solvent is distilled off under reduced pressure. To the residue is added diethyl ether, and the precipitated crystals are separated by filtration and recrystallized from 80% ethanol to give the title compound (14.9 g, yield 66.9%) as yellow prisms, m.p. 109°–111° C.

IR (KBr, cm$^{-1}$): 1685, 1520, 1350

NMR (DMSO, δ: ppm): 0.60–1.60 (13H, m), 2.00 (3H, s), 2.20 (3H, s), 2.70–3.00 (1H, m), 3.60–4.00 (4H, m), 5.30 (1H, s), 7.00–7.90 (5H, m), 8.35 (1H, s)

Elementary analysis for $C_{25}H_{31}N_3O_5 \cdot 1/10 C_2H_5OH$: Calcd. (%): C,66.06: H,6.95; N,9.17 Found (%): C,66.36: H,6.84: N,8.86

EXAMPLE 78

Preparation of n-octyl 2,6-dimethyl-3-propargylaminocarbonyl-4-(o-nitrophenyl)-1,4-dihydropyridine-5-carboxylate:

n-Octyl o-nitrobenzylideneacetoacetate (17.4 g, 0.05 mole) and 3-aminocrotonic propargylamide (6.9 g, 0.05 mole) are dissolved in benzene (60 ml), and the mixture is refluxed for 7 hours. The produced water is removed by azeotropic distillation. After the stoichiometric amount of water is removed, which is measured by taking the water with a moisture meter, the reaction is stopped.

After completion of the reaction, the solvent is distilled off under reduced pressure. The residue is dissolved in elution solvent [chloroform:carbon tetrachloride:ethyl formate:formic acid:ethanol (10:10:8:1:2)] (30 ml) and subjected to column chromatography [silica gel 60 Art. 9385 (Manufactured by Merck Co.), 600 g, φb 40 mm×100 cm]. The fraction containing the desired compound is regulated to pH 10 with 28% aqueous ammonia, and the organic layer is separated, washed with water, dried over anhydrous magnesium sulfate and then concentrated under reduced pressure. The residue is recrystallized from 80% ethanol to give the title compound (15.4 g, yield 67.4%) as yellow prisms, m.p. 85°–87° C.

IR (KBr, cm$^{-1}$): 1670, 1520, 1355

NMR (DMSO, δ:ppm): 0.60–1.70 (15H, m), 2.05 (3H, s), 2.22 (3H, s), 2.80–3.00 (1H, m), 3.60–4.00 (4H, m), 5.35 (1H), 7.10–8.00 (5H, m), 8.45 (1H, s)

Elementary analysis for $C_{26}H_{33}N_3O_5 \cdot 1/6 C_2H_5OH$: Calcd. (%): C,66.55; H,7.21: N,8.84 Found (%): C,66.83: H,7.13: N,8.53

EXAMPLE 79

Preparation of n-nonyl 2,6-dimethyl-3-propargylaminocarbonyl-4-(o-nitrophenyl)-1,4-dihydropyridine-5-carboxylate:

n-Nonyl o-nitrobenzylideneacetoacetate (18.1 g, 0.05 mole) and 3-aminocrotonic propargylamide (6.9 g, 0.05 mole) are dissolved in benzene (60 ml), and the mixture is refluxed for 7 hours. The produced water is removed by azeotropic distillation. After the stoichiometric amount of water is removed, which is measured by taking the water with a moisture meter, the reaction is stopped.

After completion of the reaction, the solvent is distilled off under reduced pressure. The residue is dissolved in elution solvent [chloroform:carbon tetrachloride:ethyl formate:formic acid:ethanol (10:10:8:1:2)] (30 ml) and subjected to column chromatography [silica gel 60 Art. 9385 (Manufactured by Merck Co.), 600 g, φ40 mm×100 cm]. The fraction containing the desired compound is regulated to pH 10 with 28% aqueous ammonia, and the organic layer is separated, washed with water, dried over anhydrous magnesium sulfate and then concentrated under reduced pressure. The residue is recrystallized from 80% ethanol to give the title compound (14.0 g, yield 59.2%) as yellow prisms, m.p. 55°–57° C.

IR (KBr, cm$^{-1}$): 1670, 1520, 1355

NMR (DMSO, δ: ppm): 0.60–1.70 (17H, m), 2.20 (3H, s), 2.22 (3H, s), 2.80–3.00 (1H, m), 3.60–4.00 (4H, m), 5.35 (1H, s), 7.10–8.00 (5H, m), 8.45 (1H, s)

Elementary analysis for $C_{27}H_{35}N_3O_5$: Calcd. (%): C,67.34: H,7.33; N,8.73 Found (%): C,67.25: H,7.23: N,8.72

EXAMPLE 80

Preparation of methyl 2,6-dimethyl-3-cyclopropylaminocarbonyl-4-(o-nitrophenyl)-1,4-dihydropyridine-5-carboxylate:

Methyl o-nitrobenzylideneacetoacetate (12.5 g, 0.05 mole) and 3-aminocrotonic cyclopropylamide (7.0 g, 0.05 mole) are dissolved in benzene (60 ml), and the mixture is refluxed for 7 hours. The produced water is removed by azeotropic distillation. After the stoichiometric amount of water is removed, which is measured by taking the water with a moisture meter, the reaction is stopped.

After completion of the reaction, the solvent is distilled off under reduced pressure. To the residue is added diethyl ether, and the precipitated crystals are separated by filtration and recrystallized from 80% ethanol to give the title compound (14.6 g, yield 78.9%) as yellow prisms, m.p. 160°–162° C.

IR (KBr, cm$^{-1}$): 1700, 1530, 1355

NMR (DMSO, δ: ppm): 0.20–0.70 (4H, m), 2.00 (3H, s), 2.15 (3H, s), 2.35–2.70 (1H, m), 3.30 (3H, s), 5.15 (1H, s), 7.00–7.60 (5H, m), 8.35 (1H, s)

Elementary analysis for $C_{19}H_{21}N_3O_5$: Calcd. (%): C,61.44: H,5.70: N,11.32 Found (%): C,61.17: H,5.74: N,11.25

EXAMPLE 81

Preparation of n-heptyl 2,6-dimethyl-3-cyclopropylaminocarbonyl-4-(o-nitrophenyl)-1,4-dihydropyridine-5-carboxylate:

n-Heptyl o-nitrobenzylideneacetoacetate (16.2 g, 0.05 mole) and 3-aminocrotonic cyclopropylamide (7.0 g, 0.05 mole) are dissolved in benzene (60 ml), and the mixture is refluxed for 7 hours. The produced water is removed by azeotropic distillation. After the stoichiometric amount of water is removed, which is measured by taking the water with a moisture meter, the reaction is stopped.

After completion of the reaction, the solvent is distilled off under reduced pressure. To the residue is added diethyl ether, and the precipitated crystals are separated by filtration and recrystallized from 80% ethanol to give the title compound (14.5 g, yield 63.4%) as yellow prisms, m.p. 103°–106° C.

IR (KBr, cm$^{-1}$): 1700, 1520, 1355

NMR (DMSO, δ: ppm): 0.20–1.70 (17H, m), 2.00 (3H, s), 2.22 (3H, s), 2.35–2.80 (1H, m), 3.60–4.00 (2H, m), 5.30 (1H, s), 7.10–7.80 (5H, m), 8.38 (1H, s)

Elementary analysis for $C_{25}H_{33}N_3O_5$: Calcd. (%): C,65.91: H,7.30: N,9.23 Found (%): C,65.88; H,7.40: N,9.03

Example 82

Preparation of n-octyl 2,6-dimethyl-3-cyclopropylaminocarbonyl-4-(o-nitrophenyl)-1,4-dihydropyridine-5-carboxylate:

n-Octyl o-nitrobenzylideneacetoacetate (17.4 g, 0.05 mole) and 3-aminocrotonic cyclopropylamide (7.0 g, 0.05 mole) are dissolved in benzene (60 ml), and the mixture is refluxed for 7 hours. The produced water is removed by azeotropic distillation. After the stoichiometric amount of water is removed, which is measured by taking the water with a moisture meter, the reaction is stopped.

After completion of the reaction, the solvent is distilled off under reduced pressure. To the residue is added diethyl ether, and the precipitated crystals are separated by filtration and recrystallized from 80% ethanol to give the title compound (19.1 g, yield 81.3%) as yellow prisms, m.p. 104°–106° C.

IR (KBr, cm$^{-1}$) 1700, 1520, 1360

NMR (DMSO, δ: ppm): 0.20–1.70 (19H, m), 2.00 (3H, s), 2.20 (3H, s), 2.35–2.80 (1H, m), 3.60–4.00 (2H, m), 5.27 (1H, s), 7.05–7.75 (5H, m), 8.33 (1H, s)

Elementary analysis for $C_{26}H_{35}N_3O_5$: Calcd. (%): C,66.50; H,7.51: N,8.95 Found (%): C,66.58: H,7.50: N,9.04

EXAMPLE 83

Preparation of n-nonyl 2,6-dimethyl-3-cyclopropylaminocarbonyl-4-(o-nitrophenyl)-1,4-dihydropyridine-5-carboxylate:

n-Nonyl o-nitrobenzylideneacetoacetate (18.1 g, 0.05 mole) and 3-aminocrotonic cyclopropylamide (7.0 g, 0.05 mole) are dissolved in benzene (60 ml), and the mixture is refluxed for 7 hours. The produced water is removed by azeotropic distillation. After the stoichiometric amount of water is removed, which is measured by taking the water with a moisture meter, the reaction is stopped.

After completion of the reaction, the solvent is distilled off under reduced pressure. To the residue is added diethyl ether, and the precipitated crystals are separated by filtration and recrystallized from 80% ethanol to give the title compound (19.1 g, yield 78.9%) as yellow prisms, m.p. 110°–112° C.

IR (KBr, cm$^{-1}$): 1695, 1520, 1355

NMR (DMSO, δ: ppm): 0.20–1.60 (21H, m), 2.03 (3H, s), 2.22 (3H, s), 2.40–2.80 (1H, m), 3.60–4.00 (2H, m), 5.30 (1H, s), 7.10–7.80 (5H, m), 8.41 (1H, s)

Elementary analysis for $C_{27}H_{37}N_3O_5$: Calcd. (%): C,67.05: H,7.71: N,8.69 Found (%): C,67.07: H,7.82: N,8.61

EXAMPLE 84

Preparation of methyl 2,6-dimethyl-3-cyclopentylaminocarbonyl-4-(o-nitrophenyl)-1,4-dihydropyridine-5-carboxylate:

Methyl o-nitrobenzylideneacetoacetate (12.5 g, 0.05 mole) and 3-aminocrotonic cyclopentylamide (8.4 g, 0.05 mole) are dissolved in benzene (60 ml), and the mixture is refluxed for 7 hours. The produced water is removed by azeotropic distillation. After the stoichiometric amount of water is removed, which is measured by taking the water with a moisture meter, the reaction is stopped.

After completion of the reaction, the solvent is distilled off under reduced pressure. To the residue is added diethyl ether, and the precipitated crystals are separated by filtration and recrystallized from ethanol to give the title compound (13.2 g, yield 66.0%) as yellow prisms, m.p. 239°–241° C.

IR (KBr, cm$^{-1}$): 1685, 1525, 1355

NMR (DMSO, δ: ppm): 1.00–1.90 (8H, m), 2.08 (3H, s), 2.18 (3H, s), 3.32 (3H, s), 3.60–4.10 (1H, m), 5.20 (1H, s), 7.00–7.70 (5H, m), 8.35 (1H, s)

Elementary analysis for $C_{21}H_{25}N_3O_5$: Calcd. (%): C,63.14: H,6.31: N,10.52 Found (%): C,63.18: H,6.27: N,10.27

EXAMPLE 85

Preparation of n-heptyl 2,6-dimethyl-3-cyclopentylaminocarbonyl-4-(o-nitrophenyl)-1,4-dihydropyridine-5-carboxylate:

n-Heptyl o-nitrobenzylideneacetoacetate (16.7 g, 0.05 mole) and 3-aminocrotonic cyclopentylamide (8.4 g, 0.05 mole) are dissolved in benzene (60 ml), and the mixture is refluxed for 7 hours. The produced water is removed by azeotropic distillation. After the stoichiometric amount of water is removed, which is measured by taking the water with a moisture meter, the reaction is stopped.

After completion of the reaction, the solvent is distilled off under reduced pressure. To the residue is added diisopropyl ether, and the precipitated crystals are separated by filtration and recrystallized from 80% ethanol to give the title compound (14.3 g, yield 59.1%) as yellow prisms, m.p. 164°–166° C.

IR (KBr, cm$^{-1}$): 1675, 1525, 1360

NMR (DMSO, δ: ppm): 0.60–1.80 (21H, m), 2.03 (3H, s), 2.20 (3H, s), 3.50–4.20 (3H, m), 5.35 (1H, s), 7.10–7.80 (5H, m), 8.35 (1H, s)

Elementary analysis for $C_{27}H_{37}N_3O_5$: Calcd. (%): C, 67.05: H, 7.71: N, 8.69 Found (%): C, 67.04: H, 7.81; N, 8.52

EXAMPLE 86

Preparation of n-octyl 2,6-dimethyl-3-cyclopentylaminocarbonyl-4-(o-nitrophenyl)-1,4-dihydropyridine-5-carboxylate:

n-Octyl o-nitrobenzylideneacetoacetate (17.4 g, 0.05 mole) and 3-aminocrotonic cyclopentylamide (8.4 g, 0.05 mole) are dissolved in benzene (60 ml), and the mixture is refluxed for 7 hours. The produced water is removed by azeotropic distillation. After the stoichiometric amount of water is removed, which is measured by taking the water with a moisture meter, the reaction is stopped.

After completion of the reaction, the solvent is distilled off under reduced pressure. To the residue is added diisopropyl ether, and the precipitated crystals are separated by filtration and recrystallized from 80% ethanol to give the title compound (14.8 g, yield 59.6%) as yellow prisms, m.p. 151°–153° C.

IR (KBr, cm$^{-1}$): 1675, 1520, 1355

NMR (DMSO, δ: ppm): 0.60–1.85 (23H, m), 2.03 (3H, s), 2.20 (3H, s), 3.50–4.20 (3H, m), 5.34 (1H, s), 7.10–7.75 (5H, m), 8.37 (1H, s)

Elementary analysis for $C_{28}H_{39}N_3O_5$: Calcd. (%): C,67.58: H,7.90: N,8.44 Found (%): C,67.46; H,7.94; N,8.27

EXAMPLE 87

Preparation of n-nonyl 2,6-dimethyl-3-cyclopentylaminocarbonyl-4-(o-nitrophenyl)-1,4-dihydropyridine-5-carboxylate:

n-Nonyl o-nitrobenzylideneacetoacetate (18.1 g, 0.05 mole) and 3-aminocrotonic cyclopentylamide (8.4 g, 0.05 mole) are dissolved in benzene (60 ml), and the mixture is refluxed for 7 hours. The produced water is removed by azeotropic distillation. After the stoichiometric amount of water is removed, which is measured by taking the water with a moisture meter, the reaction is stopped.

After completion of the reaction, the solvent is distilled off under reduced pressure. To the residue is added diisopropyl ether, and the precipitated crystals are separated by filtration and recrystallized from 80% ethanol to give the title compound (18.5 g, yield 72.3%) as yellow prisms, m.p. 154°–156° C.

IR (KBr, cm$^{-1}$): 1675, 1525, 1360

NMR (DMSO, δ: ppm): 0.55–1.80 (25H, m), 2.05 (3H, s), 2.19 (3H, s), 3.55–4.10 (3H, m), 5.30 (1H, s), 7.00–7.70 (5H, m), 8.33 (1H, s)

Elementary analysis for $C_{29}H_{41}N_3O_5$: Calcd. (%): C, 68.08: H, 8.08: N, 8.21 Found (%): C, 68.29: H, 8.15: N, 8.14

EXAMPLES 88 TO 105

In the same manner as described in Examples 80 to 87, the compounds are shown in Table 3 are prepared, wherein the compounds have the NO$_2$ group at ortho-position.

TABLE 3

| Ex. No. | R$^1$ | R$^2$ | M.p. (°C.) | Appearance (solvent for recrystallization) |
|---|---|---|---|---|
| 88 | cyclopropyl | —C$_2$H$_5$ | 201–203 | Orange prisms (ethanol) |
| 89 | " | —C$_3$H$_7$(n) | 209–210 | " |
| 90 | " | —C$_3$H$_7$(iso) | 199–201 | " |
| 91 | " | —C$_4$H$_9$(n) | 178–180 | Yellow prisms (ethanol) |
| 92 | " | —C$_4$H$_9$(iso) | 214–216 | " |
| 93 | " | —C$_5$H$_{11}$(n) | 169–171 | " |
| 94 | " | —C$_5$H$_{11}$(iso) | 190–192 | Orange prisms (ethanol) |
| 95 | " | —C$_6$H$_{13}$(n) | 122–124 | Yellow prisms (ethanol) |
| 96 | " | —C$_6$H$_{13}$(iso) | 164–166 | " |
| 97 | cyclobutyl | —C$_2$H$_5$ | 204–206 | Orange prisms (ethanol) |
| 98 | " | —C$_3$H$_7$(n) | 189–191 | Yellow prisms (ethanol) |
| 99 | " | —C$_3$H$_7$(iso) | 202–204 | Orange prisms (ethanol) |
| 100 | cyclobutyl | —C$_4$H$_9$(n) | 194–196 | Yellow prisms (ethanol) |
| 101 | " | —C$_4$H$_9$(iso) | 199–201 | Orange prisms (ethanol) |
| 102 | " | —C$_5$H$_{11}$(n) | 198–200 | Yellow prisms (ethanol) |
| 103 | " | —C$_5$H$_{11}$(iso) | 202–204 | " |

TABLE 3-continued

| Ex. No. | R¹ | R² | M.p. (°C.) | Appearance (solvent for recrystallization) |
|---|---|---|---|---|
| 104 | " | —C$_6$H$_{13}$(n) | 185–187 | " |
| 105 | " | —C$_6$H$_{13}$(iso) | 202–204 | " |

Experiment 1-1

Hypotensive activity:

[Method]:

Spontaneously hypertensive male rats (13–15 week age, one group: 3 rats) were used. The rats had a maximum systolic blood pressure of about 200 mmHg and a mean blood pressure of about 180 mmHg. The rats were fixed in a Howlman cage without fasting, and the femoral arterial pressure was measured by a direct method without anesthesia with a cannula which was previously inserted into the femoral artery of the animal, via a pressure transducer (MPU-0.5, manufactured by Nippon Koden K.K.). The test compounds were orally administered in the form of a suspension in 0.5% methyl cellulose solution in a dose of 10 mg/kg (in some compounds, 3 mg/kg). In the control group, only 0.5% methyl cellulose solution was administered likewise. The blood pressure was measured for 5 hours after the administration of test compounds.

[Results]:

The hypotensive activity of the test compounds (difference of the mean blood pressure before and after the administration of test compounds) is shown in Table 4.

The test compounds are shown in Example number as to the compounds of this invention, and the reference compounds A, B, C, D and E are as shown hereinbefore.

TABLE 4

| Test compd. No. (Ex. No.) | Maximum hypotension (mmHg) | Time until reaching to max. hypotension (minute) | Time for recovering ½ of max. hypotension (hour) | Recovering time (hour) |
|---|---|---|---|---|
| 1  | 78 | 30 | >5.0 | >5.0 |
| 2' | 55 | 30 | 5.0  | >5.0 |
| 3  | 91 | 30 | >5.0 | >5.0 |
| 3' | 60 | 30 | >5.0 | >5.0 |
| 5  | 70 | 15 | 5.0  | >5.0 |
| 6  | 57 | 15 | 3.5  | 5.0  |
| 7  | 45 | 30 | 5.0  | >5.0 |
| 8  | 30 | 15 | 4.0  | 5.0  |
| 43 | 68 | 15 | 2.5  | 5.0  |
| 44 | 60 | 15 | 2.5  | 4.0  |
| 45 | 15 | 15 | 0.5  | 1.5  |
| 46 | 10 | 15 | 0.5  | 1.5  |
| 47 | 32 | 30 | 2.0  | 3.0  |
| 51 | 40 | 30 | 3.0  | >5.0 |
| 52 | 12 | 15 | 0.5  | 1.0  |
| 63 | 7  | 15 | 1.0  | 1.5  |
| 64 | 57 | 30 | 2.0  | 5.0  |
| 65 | 50 | 30 | 1.5  | 2.5  |
| 68 | 5  | 15 | 0.5  | 1.0  |
| A  | 49 | 15 | 1.5  | 4.0  |
| B  | 57 | 15 | >5.0 | >5.0 |
| C  | 20 | 15 | 1.5  | 2.0  |
| E  | 5  | 15 | 0.5  | 1.0  |

[Note]:
In case of 2' and 3' the dose was 3 mg/kg.

As is shown in Table 4, among the compounds of this invention, alkyl 3-isopropylaminocarbonyl-4-(o-nitrophenyl)1,4-dihydropyridine-5-carboxylates (compounds of Example Nos. 1–3, 5–8, 43 and 44) showed particularly high hypotensive activity. Besides, the compounds of Example Nos. 1, 2, 3, 5 and 7 showed the same or more potent activity with longer duration in comparison with known 1,4-dihydropyridine compounds (Compound A: nifedipine, and Compound B: nicardipine hydrochloride).

Experiment 1-2

Hypotensive activity:

[Method]:

The hypotensive activity was measured in the same manner as described in Experiment 1-1 except that the rats were used in 3–5 rats per each group, and the test compounds were administered in a dose of 1 mg/kg (some compounds, 3 mg/kg), and the blood pressure was measured for 8 hours after the administration of test compounds.

[Results]:

The results are shown in Table 5.

TABLE 5

| Test compounds | | Maximum hypotension (mmHg) | Time until reaching to max. hypotension (minute) | Time for recovering ½ of max. hypotension (hour) | Recovering time (hour) |
|---|---|---|---|---|---|
| Ex. No. | Dose | | | | |
| 78 | 1 mg/kg | 33 | 60  | 3.0  | 5.0  |
| 79 | "       | 45 | 60  | 3.0  | 5.0  |
| 82 | "       | 48 | 180 | >8.0 | >8.0 |
| 83 | "       | 61 | 180 | >8.0 | >8.0 |

TABLE 5-continued

| Test compounds | | Maximum hypotension | Time until reaching to max. hypotension | Time for recovering ½ of max. hypotension | Recovering time |
|---|---|---|---|---|---|
| Ex. No. | Dose | (mmHg) | (minute) | (hour) | (hour) |
| A | 1 mg/kg | 55 | 30 | 2.0 | 3.0–4.0 |
| B | 3 mg/kg | 27 | 30 | 2.0 | 3.0–4.0 |

As is shown in Table 5, the compounds of this invention (compounds of Example Nos. 78–79, and 82–83) showed the same or more potent hypotensive activity with longer duration in comparison with known Compound A (nifedipine) and Compound B (nicardipine hydrochloride).

Experiment 2-1

Activity on isolated heart:

[Method]:

Japanese white rabbit (weighing 2.2–2.5 kg) was anesthetized by introvenous injection of nembutal (20 mg/kg) and then sacrificed by bleeding from common carotid artery. Immediately, the heart was isolated and fixed to a Rangendorff's heart perfusion apparatus (KN-206 type, manufactured by Natsume Seisakusho, Japan) and perfused by Krebs-Henseleite solution (32°±0.5° C., 95% $O_2$+5% $CO_2$) at a constant pressure of 45 cm $H_2O$. After stabilizing the heart preparation for 90 minutes, the test compound was administered. There were measured the perfusion volume with a drop-counting meter (ET-600G type, manufactured by Nippon Koden K.K.) and the heart pulse and the contractility via a force-displacement transducer (FD pick up, SB-IT type, manufactured by Nippon Koden K.K.) (for measuring heart pulse, an instant pulse meter (AT-601G type, minufactured by Nippon Koden K.K.) being further used).

The test compounds were dissolved in ethanol, and the solution was diluted in 100-fold with purified water, and the diluted solution was administered in an amount of 0.1 ml/heart (i.e. 3 μg/heart).

The results of the test in the isolated heart sample are shown in Table 6.

TABLE 6

| Test Compd No. (Ex. No.) | Increase of coronary perfusion (%) | Reducing rate of heart pulse (%) | Inhibitory rate of systole (%) |
|---|---|---|---|
| 1 | 25 | 15 | 40 |
| 2 | 17 | 25 | 50 |
| 3 | 40 | 20 | 55 |
| 5 | 28 | 25 | 15 |
| 6 | 35 | 13 | 25 |
| 7 | 45 | 25 | 30 |
| 8 | 35 | 5 | 13 |
| 40 | 25 | 1 | 14 |
| 43 | 35 | 40 | 35 |
| 44 | 30 | 16 | 20 |
| 45 | 0 | 0 | 0 |
| 46 | 14 | 3 | 9 |
| 47 | 35 | 11 | 5 |
| 51 | 40 | 25 | 30 |
| 52 | 20 | 15 | 45 |
| 62 | 20 | 6 | 2 |
| 64 | 12 | 4 | 0 |
| 65 | 8 | 8 | 5 |
| 66 | 16 | 13 | 15 |
| 68 | 29 | 11 | 6 |
| A | 40 | 10 | 35 |
| B | 15 | 5 | 10 |
| C | 16 | 7 | 17 |
| D | 20 | 5 | 15 |

TABLE 6-continued

| Test Compd No. (Ex. No.) | Increase of coronary perfusion (%) | Reducing rate of heart pulse (%) | Inhibitory rate of systole (%) |
|---|---|---|---|
| E | 0 | 1 | 0 |

As is shown in Table 6, the components of this invention (compounds of Example Nos. 3, 5 and 7) showed the same or more potent coronary vasodilating activity with longer duration in comparison with known 1,4-dihydropyridine compounds (nifedipine and nicardipine hydrochloride, etc.). Besides, the compounds of Example Nos. 1, 2, 3, 7 and 52 showed also moderate inhibitions on the heart pulse and contactility, and hence, these are also useful for the treatment of the diseases accompanied with arrhythmia or angina pectoris.

Experiment 2-2

Activity onto the isolated heart:

The activity was measured in the same manner as described in Experiment 2-1 except that in some test compounds, the dose was in 1 μg/heart. Besides, the duration of the activity was evaluated by counting the time until the coronary perfusion volume became to the initial level before the administration of the test compound.

[Results]:

The results are shown in Table 7.

TABLE 7

| Test Compd. No. (Ex. No.) | Coronary perfusion | | Reducing rate of heart pulse (%) | Inhibitory rate of systole (%) |
|---|---|---|---|---|
| | Increase (%) | Duration (minute) | | |
| 78* | 55 | 60 | 10 | 35 |
| 79* | 50 | 60 | 30 | 40 |
| 80 | 25 | <10 | 5 | 15 |
| 81 | 15 | 10–15 | 0 | 15 |
| 82 | 39 | >120 | 25 | 30 |
| 83 | 42 | >120 | 20 | 50 |
| 84* | 30 | 20–30 | 20 | 15 |
| 86* | 50 | 60 | 20 | 15 |
| 87* | 40 | 60 | 5 | 15 |
| 88 | 35 | <10 | 30 | 30 |
| 89 | 30 | <10 | 30 | 35 |
| 90 | 15 | <10 | 5 | 10 |
| 91 | 20 | <10 | 10 | 35 |
| 92 | 10 | <10 | 5 | 10 |
| 93 | 20 | 20 | 15 | 20 |
| 94 | 15 | <10 | 0 | 10 |
| 95 | 20 | 10–15 | 10 | 15 |
| 96 | 20 | <10 | 0 | 10 |
| A | 40 | <10 | 10 | 35 |
| B | 15 | <10 | 5 | 10 |

[Note]: *These were used in a dose of 1 μg/heart.

As is shown in Table 7, the compounds of this invention (compounds of Example Nos. 78–84 and 86–96) showed potent coronary vasodilating activity. Particularly, the compounds of Example Nos. 78, 79, 82–84, 86 and 87 showed more potent coronary vasodilating activity with longer duration in comparison with known Compound A (nifedipine) and Compound B (nicardipine hydrochloride), and further showed also temperate inhibitions on the heart pulse and contactility, and hence, these are also useful for the treatment of arrhythmia or angina pectoris accompanied with arrhythmia.

Experiment 3

Relaxing activity on the isolated aorta:

[Method]:

Japanese white rabbit (weighing 2.3-2.7 kg) was sacrificed by bleeding from common carotid artery. Immediately, the aorta was isolated and cut into a sprial strip. The strip preparation was vertically suspended under a resting tension of 2.0 g in a tissue bath containing 20 ml of modified Ringer solution while bubbling with a mixture of 95% $O_2$+5% $CO_2$ by connecting one end of the strip to a lever of the above-mentioned FD pick up. The aortic strip was contracted with 30 mM KCl. When the contraction became constant, the test compound was accumulatively administered, and the relaxing effect was measured. After the final treatment, $10^{-47}M$ papaverine was administered and the maximum relaxation obtained thereby was taken as 100%. In comparison with the maximum relaxation obtained by papaverine, the rate of relaxation by the test compounds was evaluated, and the concentration of the test compounds for obtaining 50% relaxation ($EC_{50}$) was calculated.

The test compound was dissolved in ethanol, and the solution was diluted in 100 to $1\times10^4$ folds with a nutrient solution, and the diluted solution was administered.

[Result]:

The relaxing activity of the test compounds on the isolated aorta is shown in Table 8.

TABLE 8

| Test compd. No. (Ex. No.) | $EC_{50}$ (M) | Test compd. No. (Ex. No.) | $EC_{50}$ (M) |
| --- | --- | --- | --- |
| 1 | $5.8 \times 10^{-7}$ | 45 | $1.7 \times 10^{-7}$ |
| 2 | $3.0 \times 10^{-7}$ | 46 | $7.0 \times 10^{-8}$ |
| 3 | $1.8 \times 10^{-7}$ | 47 | $2.0 \times 10^{-8}$ |
| 5 | $2.0 \times 10^{-8}$ | 50 | $7.0 \times 10^{-7}$ |
| 6 | $1.2 \times 10^{-8}$ | 51 | $1.3 \times 10^{-7}$ |
| 7 | $1.3 \times 10^{-7}$ | 52 | $4.2 \times 10^{-7}$ |
| 8 | $3.0 \times 10^{-8}$ | 62 | $1.5 \times 10^{-7}$ |
| 9 | $6.7 \times 10^{-7}$ | 64 | $1.5 \times 10^{-7}$ |
| 10 | $4.0 \times 10^{-7}$ | 65 | $1.3 \times 10^{-7}$ |
| 11 | $3.2 \times 10^{-7}$ | 66 | $7.0 \times 10^{-8}$ |
| 16 | $6.1 \times 10^{-7}$ | 68 | $1.0 \times 10^{-7}$ |
| 18 | $7.1 \times 10^{-7}$ | 69 | $5.7 \times 10^{-7}$ |
| 19 | $8.8 \times 10^{-7}$ | 82 | $4.4 \times 10^{-7}$ |
| 33 | $3.1 \times 10^{-8}$ | 83 | $2.9 \times 10^{-7}$ |
| 39 | $4.0 \times 10^{-8}$ | | |
| 41 | $1.3 \times 10^{-7}$ | A | $4.1 \times 10^{-8}$ |
| 42 | $3.8 \times 10^{-7}$ | B | $1.9 \times 10^{-8}$ |
| 43 | $1.8 \times 10^{-8}$ | C | $>10^{-6}$ |
| 44 | $1.7 \times 10^{-8}$ | E | $>10^{-6}$ |

As is shown in Table 8, the compounds of this invention (compounds of Example Nos. 5, 6, 8, 33, 39, 43, 44, 46, 47 and 66) showed the same or more potent activity as the known 1,4-dihydropyridine compounds (nifedipine and nicardipine hydrochloride, etc.). Besides, the compounds of Example Nos. 1, 2, 3, 7, 82 and 83 showed somewhat weak vasodilating activity but potent hypotensive activity as shown in Tables 4 and 5. Thus, these compounds may have also other hypotensive activities.

Experiment 4-1

Acute toxicity:

Wistar male rats (5 week age, weighing 105-135 g) were used. The compounds of Example Nos. 2, 3 and 7 were each orally administered to the animals in the form of a suspension in 0.5% methyl cellulose solution. The animals were observed for 7 days, and the 50% lethal dose (LD50) was calculated. The results are shown in Table 9.

TABLE 9

| Test compd. No. (Example No.) | $LD_{50}$ (mg/kg) | |
| --- | --- | --- |
| 2 | 100> | >10 |
| 3 | 1000> | >500 |
| 7 | >1000 | |

Experiment 4-2

Acute toxicity:

Wistar male and female rats (4 week age) and ddy male and female mice (4 week age) were used. The compounds of Example Nos. 82 and 83 were each orally administered to cellulose solution. The animals were observed for 7 days, and the 50% lethal dose ($LD_{50}$) was calculated. The results are shown in Table 10.

TABLE 10

| | $LD_{50}$ (mg/kg) | | | |
| --- | --- | --- | --- | --- |
| Test compd. No. | Rats | | Mice | |
| (Example No.) | Male | Female | Male | Female |
| 82 | 320 | 50 | 1280 | 1140 |
| 83 | 500> >100 | 10≧ | — | — |

What is claimed is:

1. A compound of the formula:

wherein $R^1$ is isopropyl, an allyl, propargyl, or a cycloalkyl having 3 to 8 carbon atoms, and $R^2$ is an alkyl selected from the group consisting of n-heptyl, n-octyl, n-nonyl and n-decyl.

2. The compound according to claim 1 wherein the $NO_2$ substituent is in the ortho-position.

3. The compound according to claim 1 wherein $R^2$ is n-heptyl, n-octyl, or n-nonyl.

4. The compound according to claim 1 wherein $R^1$ is cyclopropyl or cyclopentyl.

5. The compound according to claim 4 wherein $R^2$ is n-heptyl, n-octyl or n-nonyl.

6. The compound according to claim 1 wherein $R^1$ is an allyl or propargyl and $R^2$ is n-heptyl, n-octyl or n-nonyl.

7. A pharmaceutical composition having vasodilatory activity for the prophylaxis and treatment of circulatory diseases, which comprises as an active ingredient an effective amount of a compound of the formula:

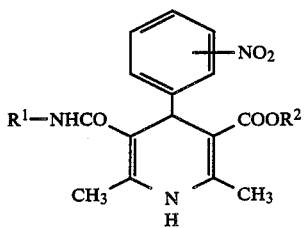

wherein R¹ is isopropyl, an allyl, propargyl, or a cycloalkyl having 3 to 8 carbon atoms, and R² is an alkyl selected from the group consisting of n-heptyl, n-octyl, n-nonyl and n-decyl, in admixture with a pharmaceutically acceptable carrier or diluent.

8. The composition according to claim 7 wherein the NO₂ substituent is in the ortho-position.

9. The pharmaceutical composition according to claim 7 wherein R² is n-heptyl, n-octyl or n-nonyl.

10. The pharmaceutical composition according to claim 7 wherein R¹ is cyclopropyl or cyclopentyl.

11. The pharmaceutical composition according to claim 10 wherein R² is n-heptyl, n-octyl or n-nonyl.

12. The pharmaceutical composition according to claim 7 wherein R¹ is allyl or propargyl and R² is n-heptyl, n-octyl or n-nonyl.

* * * * *